(12) United States Patent
Laquerre et al.

(10) Patent No.: US 6,723,316 B2
(45) Date of Patent: Apr. 20, 2004

(54) HERPES SIMPLEX VIRUS-1 GLYCOPROTEIN C MUTANTS FOR TREATING UNWANTED HYPERPROLIFERATIVE CELL GROWTH

(75) Inventors: Sylvie Laquerre, Danville, CA (US); Terry Hermiston, Corte Madera, CA (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/741,127

(22) Filed: Dec. 18, 2000

(65) Prior Publication Data

US 2002/0054885 A1 May 9, 2002

Related U.S. Application Data

(60) Provisional application No. 60/173,007, filed on Dec. 22, 1999.

(51) Int. Cl.$^7$ .................. A61K 35/76; A01N 63/00; C12N 7/01
(52) U.S. Cl. .................. 424/93.2; 424/93.6; 424/199.1; 424/205.1; 424/231.1; 435/235.1
(58) Field of Search ................ 424/93.2, 93.6, 424/199.1, 205.1, 231.1; 435/235.1

(56) References Cited

U.S. PATENT DOCUMENTS 5,728,379 A * 3/1998 Martuza et al.
5,998,174 A * 12/1999 Gloriso et al. ............. 435/91.4
6,379,674 B1 * 4/2002 Rabkin et al. ........... 424/199.1

FOREIGN PATENT DOCUMENTS

WO    WO 99/07394    2/1999

OTHER PUBLICATIONS

Lubinski et al. (Journal of Virology 72(10): 8257–8263, 1998).*

Sunstrum et al (Virus Research 11: 17–32, 1988).*

Lubinski et al (Journal of Experimental Medicine 11:1637–1646, Dec. 6, 1998).*

Sunstrum et al. "Pathogenicity of glycoprotein C negative mutants of herpes . . . " Virus Research, 11 (1988) 17–32.*

Lubinsky et al. "In vivo role of complement–interacting domains of herpes . . . " J. Exp. Med. vol. 190, No. 11, Dec. 6, 1999, 1637–1646.*

* cited by examiner

Primary Examiner—Mary E. Mosher
(74) Attorney, Agent, or Firm—Gregory Giotta

(57) ABSTRACT

The present invention relates to pharmaceutical compositions, kits, and methods of use thereof, comprising, a mutant human herpes simplex virus, which is cytopathic to susceptible target cells, such as neoplastic cells. Preferably, the virus does not produce a functionally active wild-type gC polypeptide coded for the UL44 gene.

10 Claims, 6 Drawing Sheets

HERPES SIMPLEX VIRUS-1 GLYCOPROTEIN C MUTANTS FOR TREATING UNWANTED HYPERPROLIFERATIVE CELL GROWTH

This application claims priority from U.S. priority from U.S. provisional Application No. 60/173,007, filed Dec. 22, 1999.

FIELD OF THE INVENTION

The invention described herein presents certain herpes simplex virus-1 mutants for treating unwanted hyperproliferative cell growth.

BACKGROUND OF THE INVENTION

From the early part of this century, viruses have been used to treat cancer. The approach has been two-fold; first, to isolate or generate oncolytic viruses that selectively replicate in and kill neoplastic cells, while sparing normal cells. Here investigators initially used wild type viruses, and this approach met with some, albeit, limited success. While oncolysis and slowing of tumor growth occurred with little or no damage to normal tissue, there was no significant alteration in the course of the disease. See, Smith et al., Cancer 9: 1211–1218 (1956), Cassel, W. A. et al., Cancer 18: 863–868 (1965), Webb, H. E. et al., Lancet 1: 1206–1209 (1966). See, also, Kenney, S and Pagano, J. J. Natl. Cancer Inst., vol. 86, no. 16, p.1185 (1994).

More recently, and because of the reoccurrence of disease associated with the limited efficacy of the use of wild type viruses, investigators have resorted to using recombinant viruses that can be delivered at high doses, and that are replication competent in neoplastic but not normal cells. Such viruses are effective oncolytic agents in their own right, and further, can be engineered to carry and express a transgene that enhances the anti neoplastic activity of the virus. An example of this class of viruses is an adenovirus that is mutant in the E1B region of the viral genome. See, U.S. Pat. No. 5,677,178, and Bischoff, J. R., D. H. Kirn, A. Williams, C. Heise, S. Horn, M. Muna, L. Ng, J. A. Nye, A. Sampson-Johannes, A. Fattaey, and F. McCormick. 1996, Science. 274:373–6.

It is important to distinguish the use of replication competent viruses, with or without a transgene for treating cancer, from the second approach that investigators have used to treat cancer, which is a non-replicating virus that expresses a transgene. Here the virus is used merely as a vehicle that delivers a transgene which, directly or indirectly, is responsible for killing neoplastic cells. This approach has been, and continues to be the dominant approach of using viruses to treat cancer. It has, however, met with limited success, and it appears to be less efficacious than replicating viruses.

As mentioned above, to avoid damage to normal tissues resulting from the use of high dose viral therapy it is preferred that the virus have a mutation that facilitates its replication, and hence oncolytic activity in tumor cells, but renders it essentially harmless to normal cells. This approach takes advantage of the observation that many of the cell growth regulatory mechanisms that control normal cell growth are inactivated or lost in neoplastic cells, and that these same growth control mechanisms are inactivated by viruses to facilitate viral replication. Thus, the deletion or inactivation of a viral gene that inactivates a particular normal cell growth control mechanism will prevent the virus from replicating in normal cells, but such viruses will replicate in and kill neoplastic cells that lack the particular growth control mechanism.

A further viral therapy of cancer approach takes advantage of the capacity of factors present in neoplastic cells to compensate for the deleted function(s) of a viral gene while a normal cell, which would not express these factors, would not compensate for this (these) essential viral function(s).

The use of genetically engineered replication-competent herpes simplex virus-type 1 (HSV-1) has been reported as an anti-tumor agent. See, Martuza et al., Science 252: 854 (1991). Specifically, it was shown that HSV-1 thymidine kinase-deficient mutant, dlsptk, exhibited anti-tumor activity towards human malignant glioma cells in an animal brain tumor model. Unfortunately, the HSV-1 dlsptk virus produced significant encephalitis at the doses required to kill the tumor cells adequately. See, Markert et al., Neurosurgery 32: 597 (1993).

U.S. Pat. No. 5,585,096 describes a mutated, replication-competent herpes simplex virus-type 1 (HSV-1) which contains mutations in two genes, is sensitive to antiviral agents such as acyclovir, is not neurovirulent and does not replicate in non-dividing cells, yet can kill nervous system tumor cells. This herpes simplex virus mutant is incapable of expressing both a functional gamma 34.5 gene product and ribonucleotide reductase.

U.S. Pat. No. 5,728,379 describes a method for killing tumor cells in vivo with a replication competent herpes simplex virus by the regulated expression of an essential immediate-early viral gene product.

U.S. Pat. No. 5,804,413 describes cell lines that express complementing levels of certain herpes simplex virus essential immediate early proteins Although progress has been made in identifying and using viruses for treating disease, particularly cancer, there is obviously still a great need for more effective viruses.

SUMMARY OF THE INVENTION

An aspect of the invention is the description of a method for treating unwanted hyperproliferative cell growth in a cell population with an amount of a mutant herpes simplex-1 virus that kills the cells, wherein the virus does not produce a functionally active wild-type Glycoprotein C (gC) coded for by the UL44 gene.

Another aspect of the invention is the description of a method for killing neoplastic cells with little effect on normal cells by administration of an effective amount of a mutant human herpes simplex virus, wherein the virus does not produce a functionally active wild-type Glycoprotein C (gC) coded for by the UL44 gene.

Yet another aspect of the invention is a description of methods for generating herpes simplex virus type-1 that does not produce a functionally active wild-type Glycoprotein C (gC) coded for by the UL44 gene.

An additional aspect of the invention is the description of a herpes simplex-1 glycoprotein C mutant, gC-39, that is effective for killing neoplastic cells with little, or no effect on normal cells.

A further aspect of the invention is the description of pharmaceutical compositions consisting of a mutant human herpes simplex virus, wherein the virus does not produce a functionally active wild-type Glycoprotein C (gC) coded for by the UL44 gene.

Still another aspect of the invention is the description of herpes simplex type-1 virus that does not produce a functionally active wild-type Glycoprotein C (gC) coded for by the UL44 gene and methods of using the virus to treat cancer in combination with a chemotherapeutic.

These and other aspects of the invention will become apparent upon a full consideration of the disclosure set forth herein.

DESCRIPTION OF THE INVENTION

Figure 1:
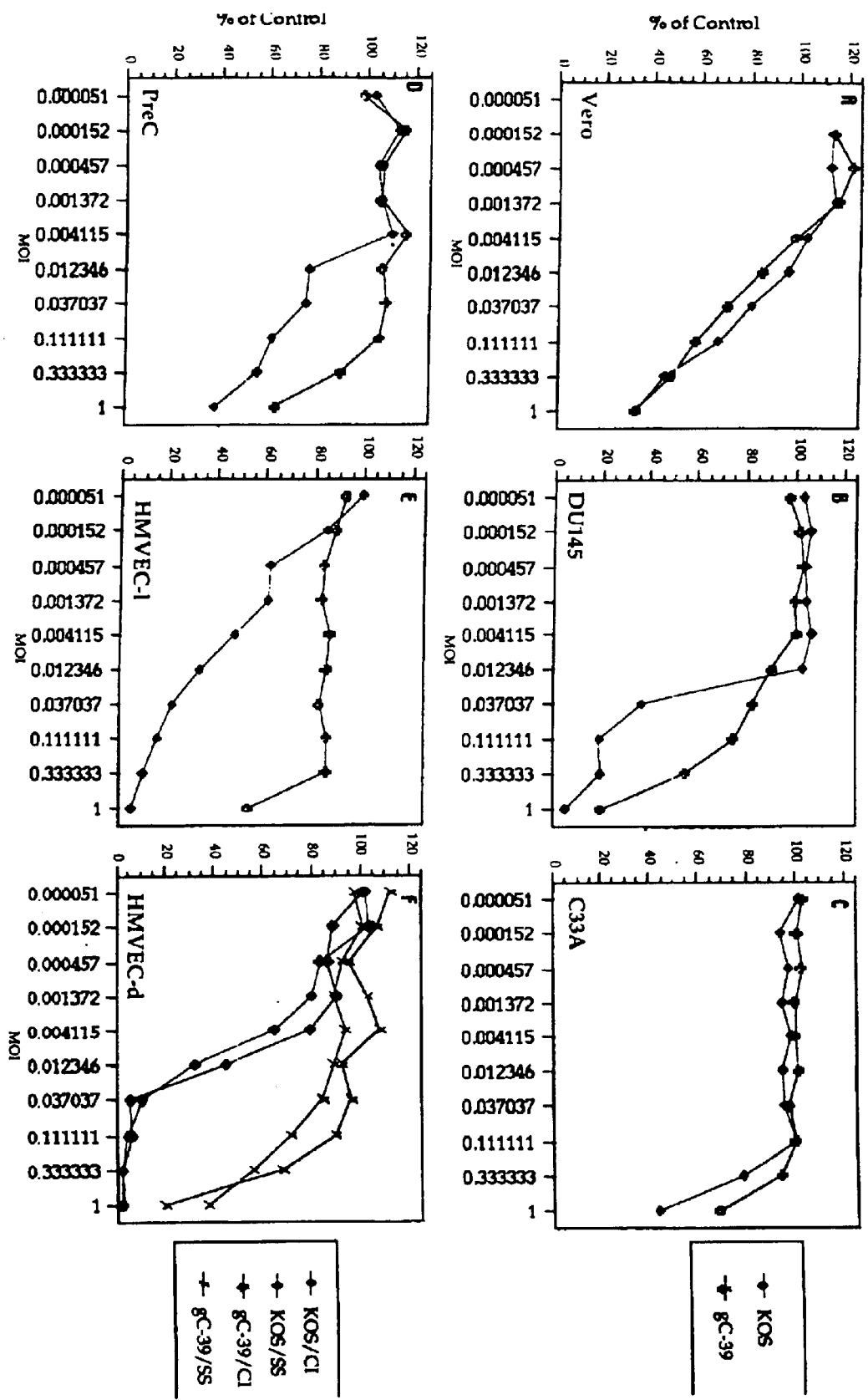
FIG. 1. Comparison of the lytic capacity of wild type KOS and gC-39 viruses on cancer and normal cell lines. Serial dilutions of HSV-1 strain KOS and its gC deleted derivative (gC-39) were used to infect cell monolayers of transformed monkey cells (Vero, panel A), prostate (DU145, panel B), cervical (C33A, panel C) and primary human quiescent prostate, (panel D), microvascular from lung (HMVEC-1, panel E) and skin (HMVEC-d, panel F) in a 96 well format. Three (panels A, B and C) and 6 (panels D, E and F) days post infection MTT assays were performed. The average of quadruplet virus dilutions were performed plotted in percentage of uninfected control cell monolayer.

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual*, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

The term "hyperproliferative cell growth" or "hyperproliferative cell" refers to a disease state characterized by an abnormal or pathological proliferation of cells, for example, neoplasia.

As used herein, "neoplastic cells" and "neoplasia" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly differentiated phenotype, or a mixture of both type of cells. Thus, not all neoplastic cells are necessarily replicating cells at a given timepoint. The set defined as neoplastic cells consists of cells in benign neoplasms and cells in malignant (or frank) neoplasms. Frankly neoplastic cells are frequently referred to as tumor cells or cancer cells, typically termed carcinoma if originating from cells of endodermal or ectodermal histological origin, or sarcoma if originating from cell types derived from mesoderm.

The term "cytopathic" encompasses any pathological or deleterious effect on a hyperproliferative cell caused by the invention herpes virus, including, lysis, apoptosis, arrest of cell growth, arrest of cell reproduction, arrest of the cell-cycle, destruction of vital organelles, such as mitochondria, nuclei, and cell membranes, DNA fragmentation, cytoplasmic blebbing, etc As used herein, "herpes" refers to herpes simplex type-1 (HSV-1) which is defined by its genome which is encoded on a linear, double-stranded DNA of about 152 kilobases, which genome has been entirely sequenced. See: McGeoch, D., et al., J. Gen. Virol. Vol. 69: 1531–1574. It will be understood, however, that while the invention herein is described in terms of glycoprotein C mutants of HSV-1 encoded by the UL 44 gene of strain KOS, that other strains of herpes that exhibit mammalian cell cytotoxicity, and that encode proteins with biological activity similar to glycoprotein c of strain KOS, can be used in the invention by mutating or deleting the gene that encodes the biologically similar protein to render it inactive.

As used herein, "physiological conditions" refers to an aqueous environment having an ionic strength, pH, and temperature substantially similar to conditions in an intact mammalian cell or in a tissue space or organ of a living mammal. Typically, physiological conditions comprise an aqueous solution having about 150 mM NaCl (or optionally KCl), pH 6.5–8.1, and a temperature of approximately 20–45° C. Generally, physiological conditions are suitable binding conditions for intermolecular association of biological macromolecules. For example, physiological conditions of 150 mM NaCl, pH 7.4, at 37° C. are generally suitable.

The present invention relates to herpes simplex type viruses 1 (HSV-1) which comprise mutations in at least one gene coding for a glycoprotein, preferably glycoprotein C (gC), or a gene which mediates viral attachment to a cell, and/or inhibition of complement mediated virus neutralization. These viruses are able to infect and lyse cells, making them useful as therapeutic, production, and research tools. In preferred embodiments, the viruses selectively disable a specific type of a target cell in a mixed population, facilitating its selective elimination from the total cell population. The target cells are preferably neoplastic cells, or other cells exhibiting cell cycle disease. Thus, for example, the viruses are useful in treating cancer, preferably by causing the cancer cells, but not normal cells, to undergo oncolysis or other cytopathic effects.

A preferred embodiment of the invention relates to a method for treating, or prophylaxis of, a neoplasm comprising cells, comprising administering to the neoplasm an amount of a mutant human herpes simplex virus which is cytopathic and/or oncolytic to cells, where the virus does not produce a functionally active glycoprotein C coded for by the UL44 gene.

Any neoplasm can be treated with the viruses as long as it susceptible to its cytopathic/lytic effect. Whether a neoplasm is susceptible to the viral effect can be determined routinely, e.g., as shown in the examples below. For instance, cells from either a primary or established cell line can be placed in an in vitro culture and contacted with varying amounts of virus (e.g., serial dilutions). Several days after infection, the cells can be assayed for viability and/or cell death to determine whether lysis has occurred. Viability and/or cell death assays can be accomplished routinely, e.g., by MTT assay as described by Promega Corporation using its commercial kit, Cell Titer 96™. See also, Korneniewski, C. and Callewaert, D. M. (1983) J. Immunol. Methods 64, 313, and Decker, T. and Lohmann-Matthes, M.-L (1988) J. Immunol. Methods 115, 61.

As shown in the examples, neoplasms that can be treated by the invention virus include, but are not limited to, neoplasms of prostate, lung, stomach, breast, uterus, ovary, pancreas, bladder, kidney, brain, bone, blood, oropharyngeal, head and neck, esophagus, testis, cervix, thyroid, adrenal gland, lymphoma, melanoma, leukemia, myeloma, Hodgkins, carcinoma, choriocarcinoma, sarcoma, neuroblastoma, Wilms disease, benign tumors, and precancerous cells.

HSV-1 encodes at least 10 surface glycoproteins (gB, gC, gD, gE, gG, gH, gI, gJ, gK, gL, and gM), of which gB, gD, gH, and gL are essential for viral infection (Cai et al., 1988, J. Virol. 62:2596–2604, Desai et al., 1994, Virology 204:312–322, Ligas et al., 1988. J. Virol. 62:1486–1494, Roizman and Sears, 1996, In B. N. Fields, D. M. Knipe, P. M. Howley, et al. (ed.) p2231–2295). The envelope glycoproteins mediate infection of the host cell through two identifiable stages: (i) attachment to the cell surface and (ii) fusion of the viral envelope with the cell surface membrane, resulting in virus entry. Virus attachment is initiated by binding of glycoproteins B and C (gB and gC) to cell surface glucosaminoglycans (Herold et al., 1994, J. Gen. Virol. 75:1211–1222, Spear, 1993, Entry of alphaherpesviruses into cells. Semin. Virol. 4:167–180). Glycoprotein C (gC) is required for infection of particular cell surfaces (e.g., apical surface of MDCK cells (Sears et al., 1991, PNAS, 88:5087–5091), such as neuronal cell (Immergluck et al., Gen Virol 1998 79:549–59) and interacts with complement C3b which protects the virus from complement-mediated neutralization.

Viruses which are useful in the present invention preferably have a mutation in a gene involved in viral attachment or entry into a cell, such as the gene coding for glycoprotein C. The entry of HSV into cells is mediated by a number of different components of the viral and cell surface. Glycoprotein C is a heparin-binding viral protein which binds to cell-surface glycosaminoglycans (GAG), such as heparan sulfate (HS). An early step in attachment of HSV to a target cell involves the interaction of gC with HS. Subsequent steps involve other viral proteins, including gB, gD, gH, and gL, which are utilized in the further attachment and penetration of the virus particle into the cell. See, e.g., Immergluck et al., J. Gen. Virol., 79:549–559, 1998; Tal-Sbinger et al., J. Virol., 69:4471–4483, 1995.

Glycoprotein C is coded for by the gene UL44. It is 511 amino acid protein migrating at 130 000 dalton due to post-traductional modifications (glycosylations) Deletion of the gene results in impaired entry into neuronal See, e.g., Sunstrum et al., Virus Research, 11: 17–32, 1988 and the apical surface of polarized cells, see Sears AE, McGwire BS, Roizman B, Proc Natl Acad Sci USA Jun. 15, 1991;88(12) :5087–91.

In preferred embodiments of the invention, the gC polypeptide is not a functionally-active wild-type gC polypeptide. By the phrase "not a functionally-active wild-type polypeptide," it is meant that polypeptide is deficient in at least one biological activity that a normal ("wild-type") polypeptide displays. Thus, the present invention includes mutant HSV-1 gC mutants which are cytopathically-or oncolytically-effective but exhibit less gC activity than a wild-type virus, e.g., 50%, 75%, 90%, 95%, 99% less, etc.

Glycoprotein C displays a number of biological activities in various in vivo and in vitro processes, including, but not limited to, viral particle attachment to a cell susceptible to its effects; attachment to the cell-surface, e.g., through GAG, HS, or another cognate receptor; binding complement component C3b protein (Lubinski et al., J. Virol., 72:8257–8263, 1998); protection of HSV-infected cells from complement mediated-lysis.

A preferred activity is its ability to attach to the surface of a cell. This activity can be measured routinely. For instance, binding of purified gC or viral particles expressing gC can be carried out as described in, e.g., Tal-Singer et al., J. Virol., 69:4471–4483, 1995; Herold et al., J. Gen. Virol., 75:1211–1222, 1994. Binding studies using labeled virus or gC can be performed on paraformaldehyde-fixed cells to reduce the effects of viral internalization and cell loss. The binding studies can be performed using a wild-type gC (either in a purified form, partially purified form, or in the form of viral particle), or a biologically-active fragment thereof, as a control. In addition, competition studies using, e.g., gC antibodies, purified gC, or soluble heparan sulfate can be performed. Instead of direct labeling, an ELISA type assay can be carried out using gC-specific antibodies, or other binding reagents. Antibodies to gC are described in Tal-Singer et al., J. Virol., 69:4471–4483, 1995.

Binding activity can also be measured indirectly by assaying for the ability of viral particles to enter cells. Viral infectivity assays can be carried out conventionally, e.g., by identifying foci of infection (e.g., Griffiths et al., J. Gen. Virol., 79:807–812, 1998), cytopathic effect, plaque assays, etc. Assays can also be performed by staining cells for the expression of a viral protein which is expressed during infection (Sears et al., Proc. Natl. Acad. Sci., 88:5087–5091, 1991), including the expression of a cloned heterologous marker gene, such as β-galactosidase, which has been inserted into the virus.

In general, useful functional assays for gC, include, binding to complement component C3, binding to immobilized heparan, binding to uninfected cells, blocking of HSV attachment to cells, and blocking HSV infection, e.g., using HS or gC antibodies.

A preferred mutant virus in accordance with the present invention is one substantially deficient (i.e., greater than 50%, preferably greater than 75%, more preferably greater than 99%) in gC biological activity. Functional inactivation of the gene can be accomplished in any manner which is effective to knock out (i.e., eliminate) one or more functions of the UL44 gene product. For example, the wild-type gene can be modified by deleting or inserting sequence into it, preferably not in-phase, which results in a non-functional product, e.g., a truncated polypeptide. A preferred deletion is a null mutation gC-39 which has a 1.7 kB deletion of the structural gene gC and which is a mutant progeny of parental wild-type HSV-1 strain KOS. See, e.g., Holland et al., *J. Virol.*, 45:672–682, 1983. Other mutations, and methods of making them, are described in, e.g., Homa et al., *J. Virol.*, 58:281–289, 1986. Other useful gC mutants include, e.g., gC-5, gC-13, gC-3, gC-17, gC-20, gC-32, gC-40, and gC-43 as described in Sunstrum et al., *Virus Research*, 11:17–32, 1988. Another useful mutation is vSH216 (Jung et al., *Virol.*, 203:299–312, 1994) which lacks amino acids 33–123 which are involved in attachment to heparan sulfate proteoglycans. Mutations also include, e.g., point mutations, inversions, promoter mutations, etc.

A virus in accordance with the present invention can further comprise other modifications in its genome. For example, it can comprise additional DNA inserted into the UL44 gene. This insertion can produce functional inactivation of the UL44 gene and the resulting lytic phenotype, or it may be inserted into an already inactivated gene, or substituted for a deleted gene.

Any desired DNA can be inserted, including DNA that encodes selectable markers, or preferably genes coding for a therapeutic, biologically active protein, such as interferons, cytokines, chemokines, or more preferably DNA coding for a prodrug converting enzyme, including thymidine kinase (Martuza et al., *Science*, 252:854, 1991), cytosine deaminadase (U.S. Pat. No. 5,358,866), cyp450 (U.S. Pat. No. 5,688,773), and others.

Other examples of genes that encode therapeutically or biologically active proteins, or fragments thereof, include those that encode immunomodulatory proteins such as, by way of example, interleukin 2 (U.S. Pat. Nos. 4,738,927 or 5,641,665); interleukin 7 (U.S. Pat. Nos. 4,965,195 or 5,328, 988); interleukin 12 (U.S. Pat. No. 5,457,038); tumor necrosis factor alpha (U.S. Pat. Nos. 4,677,063 or 5,773,582); interferon gamma (U.S. Pat. Nos. 4,727,138 or 4,762,791); or GM-CSF (U.S. Pat. Nos. 5,393,870 or 5,391,485). Additional immunomodulatory proteins further include macrophage inflammatory proteins, including MIP-3, (See, Well, T. N. and Peitsch, M C. J. Leukoc. Biol vol 61 (5): pages 545–50,1997), and cell suicide, or apoptosis inducing proteins, including BAD and BAX. See, Yang, E., et al. Cell, vol 80, pages 285–291 (1995); and Sandeep, R., et al Cell, vol. 91, pages 231–241 (1997). Monocyte chemotatic protein (MCP-3 alpha) may also be used. A preferred embodiment gene is a chimeric gene consisting of a gene that encodes a protein that traverses cell membranes, for example, VP22 or TAT, fused to a gene that encodes a protein that is preferably toxic to neoplastic but not normal cells.

Additionally, a virus in accordance with the present invention can comprise mutations at other positions in its genome, in addition to UL44. For example, in addition to the gC mutation found in gC-39, a useful virus can also comprise other mutations, polymorphisms, or variations found in the gC-39 KOS background, preferably those which are not present in the genome of other HSV-1 strains.

A preferred modification to the invention herpes viruses is incorporating promoters that impart to the viruses an enhanced level of tumor cell specificity. Since herpes simplex virus has a wide host range and is capable of infecting most cell types, herpes simplex virus mutants of the instant invention may be targeted to specific tumor types using tumor cell-specific promoters. The term "tumor cell-specific promoter" or "tumor cell-specific transcriptional regulatory sequence" or "tumor-specific promoter" or "tumor-specific transcriptional regulatory sequence" indicates a transcriptional regulatory sequence, promoter and/or enhancer that is present at a higher level in the target tumor cell than in a normal cell. The herpes simplex virus vector of the invention is engineered to place at least one viral protein necessary for viral replication under the control of a tumor-specific promoter. Or, alternatively a gene that encodes a cytotoxic agent can be put under the control of a tumor-specific promoter. By cytotoxic agent as used here is meant any protein that causes cell death. For example, such would include ricin toxin, diphtheria toxin, or truncated versions thereof. Also, included would be genes that encode prodrugs, as discussed above, cytokines, or chemokines. Tumor-specific, HSV-1 mutants of the invention may utilize promoters from genes that are highly expressed in the targeted tumor such as the epidermal growth factor receptor promoter (EGFr) or the basic fibroblast growth factor (bFGF) promoter, or other tumor associated promoters or enhancer elements.

The construction of the invention HSV-1 mutants that lack that the ability to encode glycoprotein C, or that encode another tumor specific promoter that drives the expression of a cytotoxic protein can be generated as described, for example, in U.S. Pat. No. 5,288,641; Johnson et al., J. Virol. 66: 2952 (1992); Gage et al., J. Virol. 66: 5509 (1992); Goldstein and Weller, J. Virol. 62: 196 (1988), Coen, chapter 7, Virology, Raven Press, 1990; Breakefield and DeLuca, The New Biologist, 3:203 (1991); Leib and Olivo, BioEssays 15:547 (1993); Glorioso et al., Seminars in Virology 3:265 (1992); Chou and Roizman, Proc. Natl. Acad. Sci. USA, 89:3266 (1992); or Palella et al., Molec. Cell. Biol. 8: 457 (1988). Additional methods for the genetic manipulation of DNA sequences are known in the art. Generally, these include Ausubel et al., chapter 16 in Current Protocols in Molecular Biology (John Wiley and Sons, Inc.); See, also, U.S. Pat. No. 4,603,112 (July 1986) and Coen D. M., "Molecular Genetics of Animal Viruses," in Virology 123–150 (2nd ed.) (Raven Press, 1990).

Virus in accordance with the present invention is administered in any way suitable to achieve the desired effect. i.e., it is administered under effective conditions. In a preferred embodiment, the virus is administered in such a manner to treat a neoplasm or cancer. The virus is generally administered in an amount that is effective to produce tumor stasis or regression, preferably in an amount which produces a cytopathic effect in cells, e.g., in an amount which is oncolytic to the cells. The term "cytopathic" encompasses any pathological or deleterious effect on a cell, including, lysis, apoptosis, arrest of cell growth, arrest of cell reproduction, arrest of the cell-cycle, destruction of vital organelles, such as mitochondria, nuclei, and cell membranes, DNA fragmentation, cytoplasmic blebbing, etc. By the terms "oncolytic," it is meant that the virus produces disintegration ("lysis") in target neoplastic cells preferentially over normal cells. As shown in the examples, a mutation in accordance with the present invention displays preferential oncolytic activity on tumor cells versus primary normal cells. For example, a quantity of wild-type virus which is highly lytic to normal prostate, cervial, lung microvascular and skin cells is not highly lytic to the same cells when a virus in accordance with the present invention is used. See, e.g, FIG. 1.

Effective amounts of virus to accomplish lysis, tumor regression, tumor stasis, or other therapeutic effects can be determined routinely, e.g., by performing a dose-response experiment in which varying doses are administered to target cells to determine an effective amount in producing lysis. Amounts are selected based on various factors, including the milieu to which the virus is administered (e.g., a patient with cancer, animal model, tissue culture cells, etc.), location of cells to be treated, type of cancer and its properties, size of tumor, degree to which the disease has progressed, age, health, gender, and weight of a patient or animal to be treated, etc. Useful amounts include, e.g., $10^4$–$10^{12}$ pfu, preferably, $10^6$–$10^{10}$ pfu.

The mutant HSV viruses described herein preferably are cytopathic or lytic to neoplastic cells ("oncolytic"). Thus, it is preferred that a treatment in accordance with the invention results in lysis of the neoplastic cells. In this sense, treatment indicates that the disease is altered by eliminating neoplastic cells. Such elimination can result in tumor regression. However, treatment can also cause the tumor to stop or slow growth, without any noticeable regression. In a preferred method of the present invention, a virus is used to lyse neoplastic cells in a mixed cell population, in a host (e.g., a human with cancer, a nonhuman mammal comprising a graft of cancer cells, such as human cancer cells injected subcutaneously or intraperitaneally as in an animal model, or a non-human mammal having a spontaneous cancer, such as an oncomouse), etc.

The virus can be administered by any means suitable to achieve a therapeutic effect, e.g., by injection directly into, or close by, a tumor or cancerous growth, i.e., intratumorally, topically, enterally, parenterally, intravenously, intramuscularly, subcutaneously, orally, nasally, intracerebrally, intraventricularly, etc., e.g., depending upon the location of the target cells. See, e.g, Randazzo et al., *Virol.*, 211:94–101, 1995; Walker et al., *Human Gene Therapy*, 10:2237–2243, 1999.

Virus can be administered in any suitable form, preferably as a viral particle. However, it can also be complexed to a suitable carrier, such as calcium phosphate, DEAE-dextran complexes, lipids, polymers, etc. See, e.g., U.S. Pat. Nos. 5,976,567 and 5,962,429. The virus can be produced conventionally in culture and packaged into a mature viral particle, or naked viral DNA can be prepared and complexed to any suitable carrier, such as those mentioned above, in combination with glycoprotein C or other viral and non-viral components.

A virus in accordance with the present invention can be administered with any other therapy useful to treat a neoplasm, cancer, or other cell cycle disease. Including, e.g., surgery, radiation, and chemotherapeutic agents, such as alkylating agents (e.g., cisplatin), structural analogs or antimetabolites (e.g., methotrexate), hormonal agents (e.g., tamoxifen), androcorticosteroids (e.g., prednisone), aromatase inhibitors, GnRH analogs, biologic response modifiers (e.g., interferons), peptide hormone inhibitors, natural products (e.g., vinblastine, mitomycin), etc. See, e.g., *Current Medical Diagnosis and Treatment*, Tierney et al., ed., 1997, Pages, 81–87. Especially preferred are, flurouracil, levamisole, leucovorin, mitomymcin, carmustine, cisplatin, floxuridine, methotrexate, and radiation treatment. Such treatments and agents can be co-administered with virus, sequentially, etc. By the term "chemotherapeutic agent," it is meant any chemical agent which is useful to treat unwanted hyperproliferative disease.

A pharmaceutically acceptable carrier or excipient may be used to deliver the virus. A variety of aqueous solutions can be used, e.g., water, buffered water, 0.4% saline, 0.3% glycine proteins and the like. These solutions are sterile and generally free of particulate matter other than the desired herpes viral vector. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by herpes virus may be included.

Chemotherapy may be administered by methods well known to the skilled practitioner, including systemically, direct injection into the cancer, or by localization at the site of the cancer by associating the desired chemotherapeutic agent with an appropriate slow release material or intraarterial perfusing the tumor. The preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50–120 mg/m$^2$ over 3–6 hours. More preferably it is administered intravenously at a dose of 80 mg/m$^2$ over 4 hours. A second chemotherapeutic agent, which is preferably administered in combination with cisplatin is 5-fluorouracil. The preferred dose of 5-fluorouracil is 800–1200 mg/m$^2$ per day for 5 consecutive days.

The present invention also relates to pharmaceutical compositions comprising an effective amount of a virus in accordance with the present invention, e.g., where the virus is in a form for therapeutic use. In addition, the invention relates to kits comprising a mutant human herpes simplex virus which is lytic to cells in said neoplasm, wherein said virus does not produce a functionally active wild-type gC polypeptide coded for by the UL44 and a chemotherapeutic agent, such as those mentioned above.

The following examples are presented to illustrate the present invention and to assist one of ordinary skill in making and using the same. The examples are not intended in any way to otherwise limit the scope of the disclosure or the protection granted by Letters patent hereon.

EXAMPLES

Example 1

Effect of HSV-1 Glycoprotein C Mutant, gC-39, on Human Cancer and Normal Cells

Here we show that a gC deleted virus (gC-39) (Holland et al., 1984, J. Virol. 52:566–574), displayed potency equal to the wt KOS virus (parental virus) on African green monkey kidney, that is, Vero cells (FIG. 1A), and was slightly attenuated compared to KOS on several cancer cell lines (FIGS. 1B and C). However, the lytic effect of gC-39 virus on several primary cell lines was greatly diminished (FIGS. 1D, E and F) (up to 1000×), especially on quiescent human microvascular endothelial cells of lung (HMVEC-1) of dermal origin (HMVEC-d) (FIG. 1F).

In order to quantitatively determine the lytic capacity of HSV, as described above, we developed a cell-based assay in a 96 well format. In this assay, the lytic capacity of virus A is compared to that of virus B. The assay is done in quadruplicate starting at an MOI of 1.0 (as determined by titration on Vero cells) with successive 3 fold dilutions used to infect successive wells. Three to 6 days PI, the lytic capacity of each virus is determined by MTT and expressed as percentage of control (uninfected cells) for each virus dilution. MTT is a colorimetric assay where the cellular conversion of a tetazolium salt substrate into a formazan product is taken as a measure of the cell viability. The more efficient the virus is at lysing the target cell, the less substrate is converted in the product which is monitored at 570 nm.

Example 2

Figure 2A:
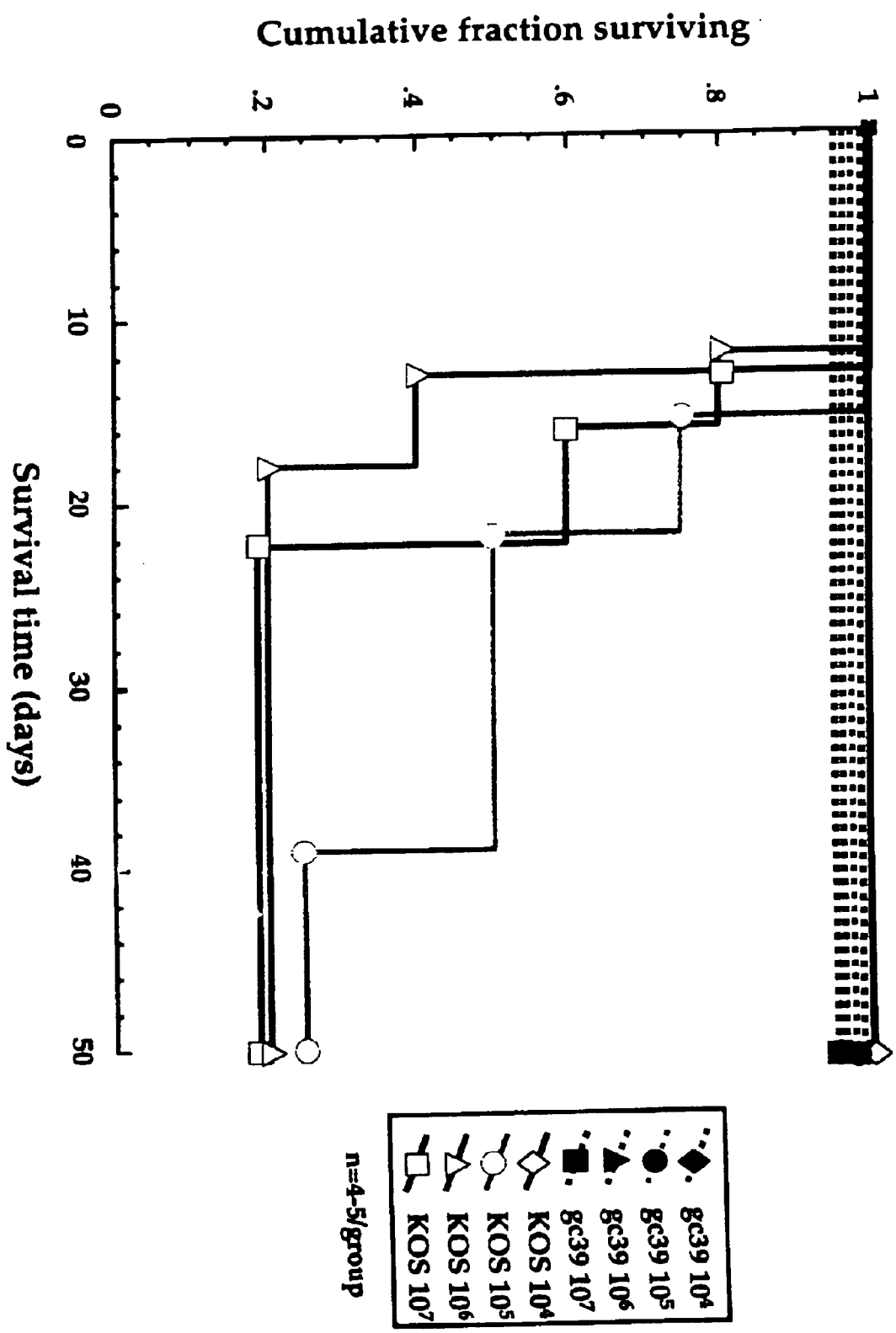
FIG. 2. Animal survival and tumor volume following intravenous injection of wild-type KOS and gC-39 mutant viruses. Viral titers of $1 \times 10^4$, $1 \times 10^5$, $1 \times 10^6$, and $1 \times 10^7$ pfus of wild-type KOS and gC-39 viruses were intravenously injected (tail vein) into nude mice bearing HT-29 xenograft tumors. A) Survival graphs were plotted on day 50, determined as a percentage of animals (n=5/group) surviving viral challenge. B) Individual tumor volume (mm3) were plotted for each animal from all different groups.
Figure 2B:
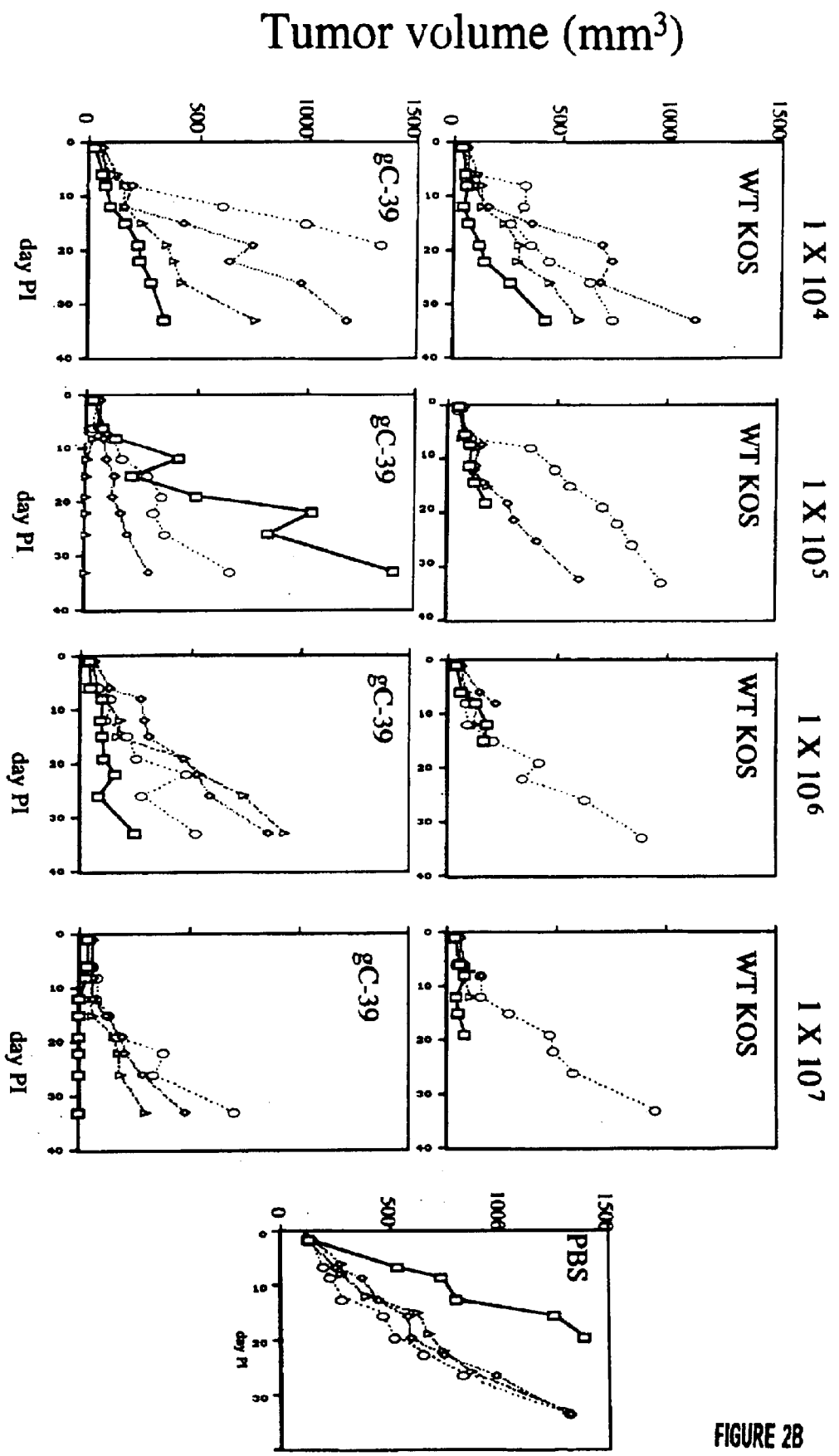
Figure 3:
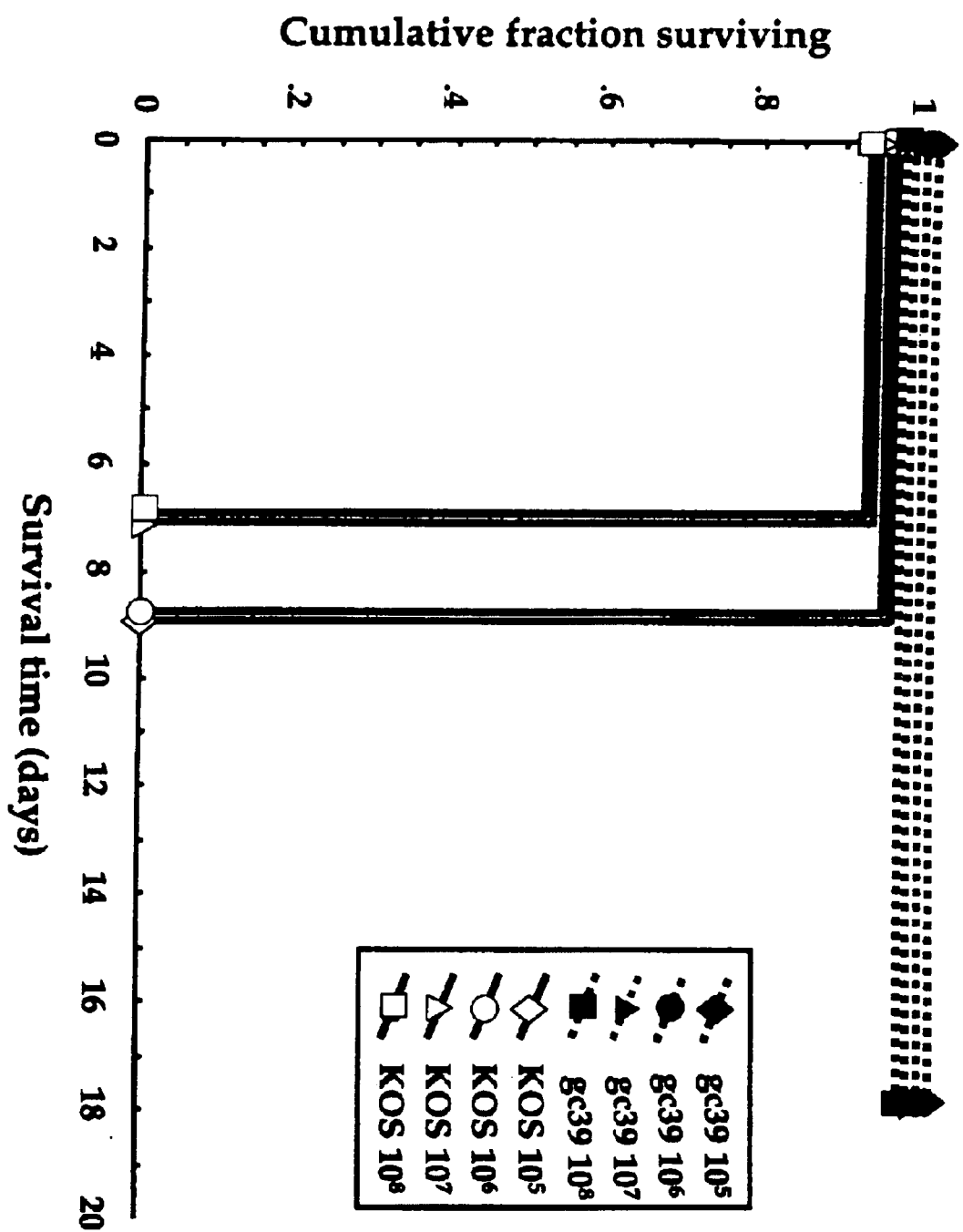
FIG. 3. Animal survival following intravenous injection of wild-type KOS and gC39 mutant viruses. Viral titers of $1 \times 10^5$, $1 \times 10^6$, $1 \times 10^7$ and $1 \times 10^8$ pfus of wild-type KOS and gC-39 viruses were intravenously injected (tail vein) into immunocompetent Balb/c mice. Survival graphs were plotted on day 20, determined as a percentage of animals (n=8/group) surviving viral challenge.
Figure 4:
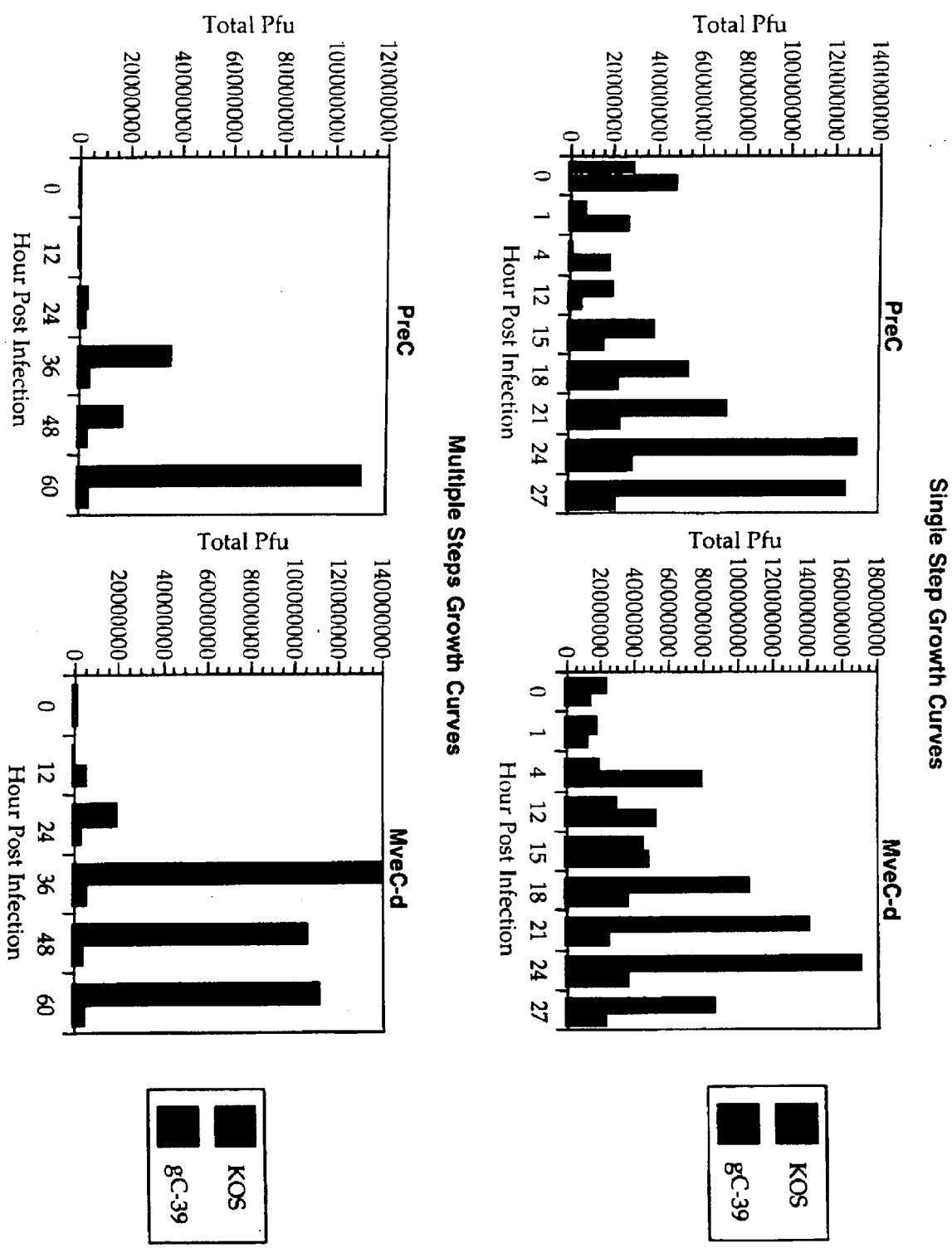
FIG. 4. Single and multiple step growth curves of wild-type KOS and gC-39 viruses on normal prostate (PreC) and microvascular from skin (MveC-d) cells. Quiescent normal cells (PreC and MveC-d) were infected at moi of 5 (single step growth curves) or 0.05 (multiple step growth curves) with wild-type KOS and gC-39 viruses. At different time points post infection viruses from supernatant and cells were harvested and titrated on Vero cells.
Figure 5:
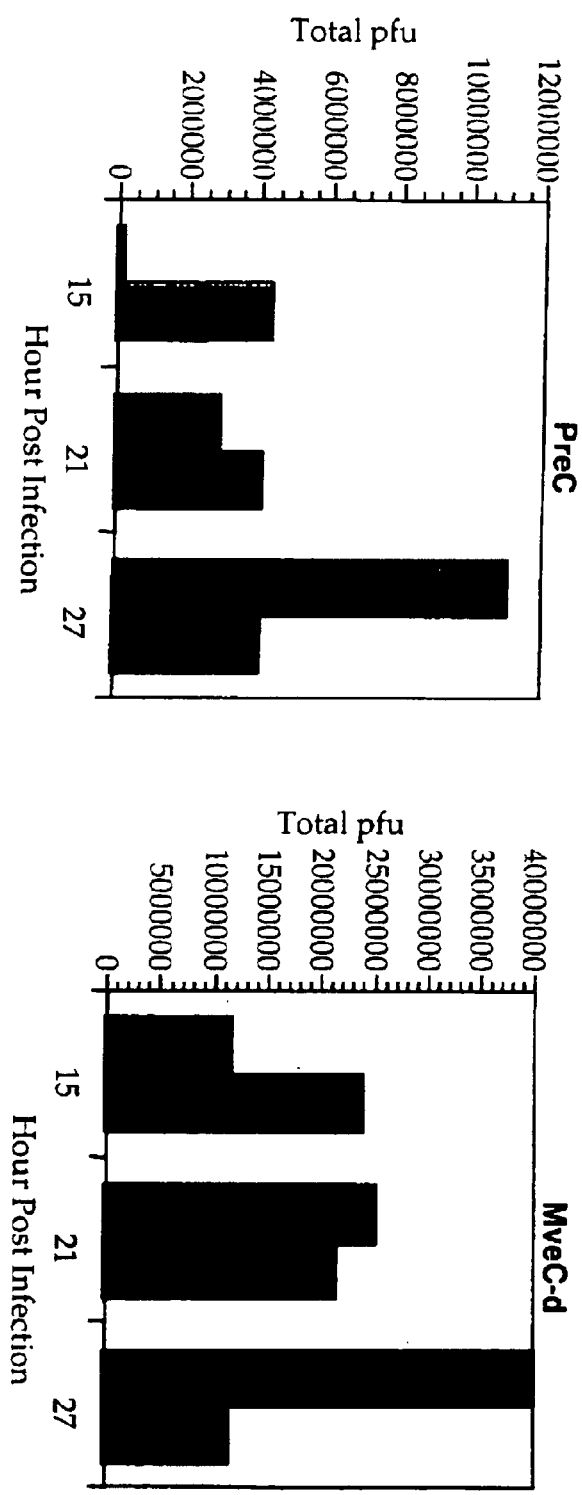
FIG. 5. Wild-type KOS and gC-39 burst size from normal cell infections. Quiescent normal cells (PreC and MveC-d) were infected at moi of 5 with wild-type KOS and gC-39 viruses. At different time points post infection viruses from supernatant only were harvested and titrated on Vero cells.

Effect of HSV-1 Glycoprotein C Mutant, gC-39, on animal survival and Tumor Volumes Preliminary animal toxicology studies demonstrated that intravenous injection of wt KOS virus to nude mice is lethal at a dose of $1 \times 10^5$ pfu (60% mortality at 22 days post injection, PI), while injection of the gC-39 virus at a dose 100× higher is not lethal after 50 days PI (FIG. 2) and produced completed tumor regression (CR) in several of the animals treated (FIG. 3). In non tumor-bearing immunocompetent BalB/C mice, a single intravenous injection of KOS was 100% lethal by day 7 ($10^7$ or $10^8$ pfu) or day 9 ($10^5$ or $10^6$ pfu). In contrast, no deaths occurred after injection of gC-39 at these doses.

Example 3

Growth Defect of gC-39 Mutant Virus in Human Normal Cells

Quiescent human normal primary cells from prostate (PreC) and from macrovascular endothelium from the skin (MveC-d) were infected at MOI of 5.0 (single step growth curves, and burst)) and 0.05 (multiple step growth curve) with wild-type KOS and gC deleted virus (gC-39). At different points (hours) post-infection, the viruses from the cells and supernatant (single and multiple growth curves) or from supernatant only (burst) were harvested and titrated on Vero cells. These data demonstrated that gC-39 virus is attenuated at the level of virus production (single step growth curve and burst) and entry (multiple step growth curve) in human normal cells while attenuated only at the level of entry on cancer cells (Laquerre et al J Virol. July 1998;72(7):6119–30.

For other aspects of the cell culture, virology, nucleic acids, polypeptides, etc., reference is made to standard textbooks. See, e.g., Davis et al. (1986), *Basic Methods in Molecular Biology*, Elsevir Sciences Publishing, Inc., New York; Hames et al. (1985), *Nucleic Acid Hybridization*, IL Press, Molecular Cloning, Sambrook et al.; *Current Protocols in Molecular Biology*, Edited by F. M. Ausubel et al., John Wiley & Sons, Inc; *Current Protocols in Protein Science*; Edited by John E. Coligan et al., John Wiley & Sons, Inc.; *Animal Cell Culture*, Freshney et al., IRL Press, 1992; *Basic Cell Culture Protocols*, Pollard and Walker, Humana Press, 1997; *General Techniques of Cell Culture*, Harrison and Rae, Cambridge University Press, 1997; *Virus Culture*, Cann, ed., Oxford University Press, 1999; *Herpes simplex Virus Protocols*, Brown and MacLean, eds., Humana Press, 1998.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patents and publications, cited throughout this patent application, and in the figures are hereby incorporated in their entirety by reference.

From the foregoing description, one skilled in the art can easily ascertain the essential characteristics of this invention, and without departing from the spirit and scope thereof, can make various changes and modifications of the invention to adapt it to various usages and conditions.

In the claims:

1. A method for treating a neoplasm comprising cells, comprising:
    administering to said neoplasm an amount of a mutant human herpes simplex virus which is oncolytic to cells in said neoplasm, wherein said virus does not produce a functionally active wild-type glycoprotein C polypeptide capable of binding heparan sulfate.

2. A method of claim 1, wherein said virus comprises a deletion in the UL44 gene which codes for heparan binding of glycoprotein C polypeptide.

3. A method of claim 1, wherein said virus comprises a deletion of amino acids 33–123 in the UL44 gene.

4. A method of claim 1, wherein said virus comprises an insertion in the UL44 gene which codes for heparan binding of glycoprotein C polypeptide.

5. A method of claim 1 wherein the parental strain of said virus is KOS.

6. A method of claim 1, wherein said virus is gC-39.

7. A method of claim 1, wherein said virus is impaired in its ability to infect, or attach to the surface of normal cells as compared to the wild-type parental strain.

8. A method of claim 1, wherein said virus is impaired in its ability to infect neuronal cells as compared to the wild-type parental strain.

9. A method of claim 1, wherein said neoplasm is anadenocarinoma.

10. A kit comprising a mutant human herpes simplex virus which is oncolytic to cells in a neoplasm, wherein said virus does not produce a functionally active wild-type glycoprotein C polypeptide capable of binding heparun sulfate and a chemotheraputic agent.

* * * * *